US011170040B2

(12) United States Patent
Rahme et al.

(10) Patent No.: US 11,170,040 B2
(45) Date of Patent: Nov. 9, 2021

(54) SYSTEM AND DEVICE FOR PRE-CACHING OF RELATED MEDICAL IMAGING

(71) Applicant: Imaging Advantage LLC, Phoenix, AZ (US)

(72) Inventors: Kamil Rahme, Phoenix, AZ (US); Jordan Kojouharov, Scottsdale, AZ (US)

(73) Assignee: Imaging Advantage LLC, Phoenix, AZ (US)

(*) Notice: Subject to any disclaimer, the term of this patent is extended or adjusted under 35 U.S.C. 154(b) by 0 days.

(21) Appl. No.: 16/860,654

(22) Filed: Apr. 28, 2020

(65) Prior Publication Data

US 2020/0257720 A1 Aug. 13, 2020

Related U.S. Application Data

(63) Continuation-in-part of application No. 15/489,993, filed on Apr. 18, 2017, now Pat. No. 10,387,196, and a continuation-in-part of application No. 15/489,996, filed on Apr. 18, 2017, now Pat. No. 10,678,850.

(60) Provisional application No. 62/324,273, filed on Apr. 18, 2016, provisional application No. 62/324,271, filed on Apr. 18, 2016.

(51) Int. Cl.
| | |
|---|---|
| *G06F 9/46* | (2006.01) |
| *G06F 16/58* | (2019.01) |
| *A61B 6/00* | (2006.01) |
| *A61B 8/00* | (2006.01) |
| *G16H 15/00* | (2018.01) |
| *G16H 30/20* | (2018.01) |

(Continued)

(52) U.S. Cl.
CPC .......... *G06F 16/5866* (2019.01); *A61B 6/563* (2013.01); *A61B 8/565* (2013.01); *G06F 9/4881* (2013.01); *G16H 15/00* (2018.01); *G16H 30/20* (2018.01); *A61B 1/00011* (2013.01)

(58) Field of Classification Search
CPC ... G06F 16/5866; G06F 9/4881; G16H 15/00; G16H 30/20; A61B 6/563; A61B 8/565; A61B 1/00011
See application file for complete search history.

(56) References Cited

U.S. PATENT DOCUMENTS

| | | | |
|---|---|---|---|
| 7,234,064 B2 | 6/2007 | Menschik et al. | |
| 7,523,505 B2 | 4/2009 | Menschik et al. | |

(Continued)

OTHER PUBLICATIONS

Google patents search on Jan. 16, 2020 "Extract metadata and site data and modality data and generating search", 2 pages.

*Primary Examiner* — Gregory A Kessler
(74) *Attorney, Agent, or Firm* — Kilpatrick Townsend & Stockton LLP

(57) ABSTRACT

Improved systems and devices for pre-caching of related medical imaging are provided. A medical imaging order may be received from a medical facility that includes medical imaging of a site generated by a medical imaging device. The medical imaging order may include metadata, such as user data, site data, and modality data. A search may be executed for supplemental medical imaging of the user using the user data. The supplemental medical imaging may be filtered using the site data to return only that medical imaging related to the site. The filtered supplemental medical imaging may be prioritized using the modality data. The prioritized supplemental medical imaging may be appended to the request, and the request may be transmitted to a radiologist for generation of a medical imaging report.

20 Claims, 9 Drawing Sheets

(51) Int. Cl.
    *G06F 9/48*     (2006.01)
    *A61B 1/00*     (2006.01)

(56) References Cited

U.S. PATENT DOCUMENTS

| | | |
|---|---|---|
| 8,108,432 B2 | 1/2012 | Westin et al. |
| 10,387,196 B2 | 8/2019 | Rahme et al. |
| 10,678,850 B2 | 6/2020 | Rahme et al. |
| 2008/0027917 A1 | 1/2008 | Mukherjee et al. |
| 2015/0154778 A1 | 6/2015 | Hughes |

SYSTEM AND DEVICE FOR PRE-CACHING OF RELATED MEDICAL IMAGING

CROSS-REFERENCES TO RELATED APPLICATIONS

This application is a continuation-in-part of U.S. patent application Ser. No. 15/489,993, filed Apr. 18, 2017, now U.S. Pat. No. 10,387,196; and is a continuation-in-part of U.S. patent application Ser. No. 15/489,996, filed Apr. 18, 2017, now U.S. Pat. No. 10,678,850; each of which claims the benefit of U.S. Provisional Patent Application No. 62/324,273, filed Apr. 18, 2016, and U.S. Provisional Patent Application No. 62/324,271, filed Apr. 18, 2016. Each of the above-referenced applications is incorporated by reference herein in its entirety for all purposes.

BACKGROUND OF THE INVENTION

Medical facilities, including hospitals and clinics, implement a variety of medical imaging systems, such as X-rays, CTs, MRIs, ultrasounds, and the like, to create medical images of patients. These medical images may be combined with patient information (e.g., name, date of birth, historical medical records, etc.) as well as imaging information (e.g., type of imaging, body location of imaging, name and location of medical facility, etc.) to create EMRs (electronic medical records). The EMRs may then be sent to radiologists, who may analyze and interpret the medical images. The radiologists may generate a medical imaging report including analysis and information (e.g., diagnoses, findings, conclusions, radiologist name, date and time of diagnoses, comments, etc.) that may be forwarded back to the medical facilities for appropriate treatment of the patients.

Implementing these processes may give rise to a variety of obstacles. For example, radiologists may desire a large number of medical images in order to generate a medical imaging report. The desired medical images may be high in resolution and large in size. Further, the desired medical images may include medical imaging of the patient that was taken at a different time than the medical imaging included in the order from the medical facility. Thus, getting the desired medical images may result in a longer turnaround time. Because the turnaround time for having the medical imaging analyzed may be critical in some cases, any delay in receiving the medical imaging report may impact patient care. Further, time lag associated with technological barriers to sharing medical imaging can increase cost of care.

SUMMARY OF THE INVENTION

Thus, according to some embodiments of the invention, improved systems and devices for pre-caching of related medical imaging are provided. According to some embodiments of the invention, a medical imaging order may be received from a medical facility that includes medical imaging (e.g., an X-ray, ultrasound, CT scan, MRI, etc.) of a site generated by a medical imaging device. The medical imaging order may include metadata, such as user data, site data, and modality data. A search may be executed for supplemental medical imaging of the user using the user data. The supplemental medical imaging may be filtered using the site data to return only that medical imaging related to the site (e.g., of the site or proximate to the site). The filtered supplemental medical imaging may be prioritized using the modality data (e.g., to show medical imaging having the same modality first). The prioritized supplemental medical imaging may be appended to the request, and the request may be transmitted to a radiologist.

According to some embodiments of the invention, a device for organizing radiological imaging queues at scale is provided. The device comprises a processor and a memory coupled to the processor. The memory stores instructions, which when executed by the processor, cause the device to perform operations including receiving, by a network interface of the device in a network, a request to generate a report file. The request includes at least one image file. The at least one image file depicts a site of the user. The at least one image file was generated by an imaging device. The request is received from a first node external to the device in the network.

The first node stores a plurality of image files including the at least one image file. The operations further include extracting metadata from the request. The metadata includes user data, site data, and modality data. The user data is associated with the user. The site data is associated with the site depicted in the at least one image file. The modality data is associated with the imaging device. The operations further include generating a search string for at least one supplemental image file of the user based on the user data. The operations further include transmitting the search string to the first node for execution on the plurality of image files. The operations further include receiving a set of results responsive to the search string from the first node, wherein the set of results includes the at least one supplemental image file of the user. The operations further include filtering the set of results using the site data to generate a subset of results. The operations further include prioritizing the subset of results based on the modality data. The operations further include appending the prioritized subset of results to the at least one image file in the request. The operations further include transmitting the request including the at least one image file and the prioritized subset of results to a second node external to the device in the network.

According to some embodiments of the invention, a computer-implemented method is provided. The method comprises receiving, by a network interface of a server in a network, a request to generate a report file. The request includes at least one image file, wherein the at least one image file depicts a site of the user. The at least one image file was generated by an imaging device. The request is received from a first node external to the server in the network. The first node stores a plurality of image files including the at least one image file. The method further comprises extracting metadata from the request. The metadata includes user data, site data, and modality data. The user data is associated with the user. The site data is associated with the site depicted in the at least one image file. The modality data is associated with the imaging device. The method further comprises generating a search string for at least one supplemental image file of the user based on the user data. The method further comprises transmitting the search string to the first node for execution on the plurality of image files. The method further comprises receiving a set of results responsive to the search string from the first node. The set of results includes the at least one supplemental image file of the user. The method further comprises filtering the set of results using the site data to generate a subset of results. The method further comprises prioritizing the subset of results based on the modality data. The method further comprises appending the prioritized subset of results to the at least one image file in the request. The method further comprises transmitting the request including the at least one image file and the prioritized subset of results to a second node external to the server in the network.

According to some embodiments of the invention, a computer-program product tangibly embodied in a non-transitory machine-readable storage medium of a computing device is provided. The non-transitory machine-readable storage medium includes instructions that, when executed by one or more processors, cause the one or more processors to receive, by a network interface of the computing device in a network, a request to generate a report file. The request includes at least one image file. The at least one image file depicts a site of the user. The at least one image file was generated by an imaging device. The request is received from a first node external to the computing device in the network. The first node stores a plurality of image files including the at least one image file. The instructions further cause the one or more processors to extract metadata from the request. The metadata includes user data, site data, and modality data. The user data is associated with the user. The site data is associated with the site depicted in the at least one image file. The modality data is associated with the imaging device. The instructions further cause the one or more processors to generate a search string for at least one supplemental image file of the user based on the user data. The instructions further cause the one or more processors to transmit the search string to the first node for execution on the plurality of image files. The instructions further cause the one or more processors to receive a set of results responsive to the search string from the first node. The set of results includes the at least one supplemental image file of the user. The instructions further cause the one or more processors to filter the set of results using the site data to generate a subset of results. The instructions further cause the one or more processors to prioritize the subset of results based on the modality data. The instructions further cause the one or more processors to append the prioritized subset of results to the at least one image file in the request. The instructions further cause the one or more processors to transmit the request including the at least one image file and the prioritized subset of results to a second node external to the computing device in the network.

This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings, and each claim.

The foregoing, together with other features and embodiments, will become more apparent upon referring to the following specification, claims, and accompanying drawings.

BRIEF DESCRIPTION OF THE DRAWINGS

Illustrative embodiments of the present invention are described in detail below with reference to the following drawing figures.

DETAILED DESCRIPTION OF THE INVENTION

Figure 1:
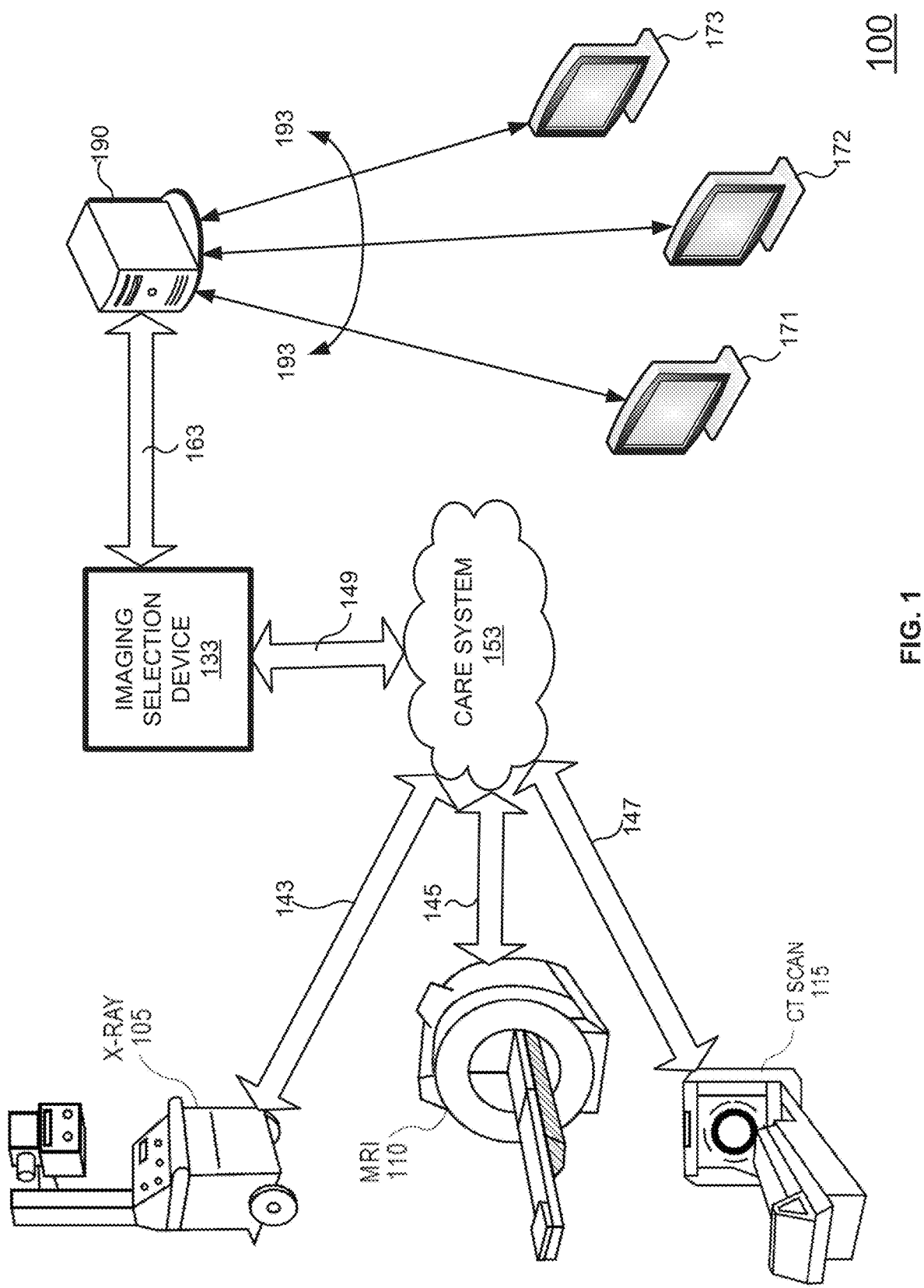
FIG. 1 is a system diagram illustrating a medical imaging distribution system according to some embodiments of the invention.

Certain aspects and embodiments of this disclosure are provided below. Some of these aspects and embodiments may be applied independently and some of them may be applied in combination as would be apparent to those of skill in the art. In the following description, for the purposes of explanation, specific details are set forth in order to provide a thorough understanding of embodiments of the invention. However, it will be apparent that various embodiments may be practiced without these specific details. The figures and description are not intended to be restrictive.

The ensuing description provides exemplary embodiments only, and is not intended to limit the scope, applicability, or configuration of the disclosure. Rather, the ensuing description of the exemplary embodiments will provide those skilled in the art with an enabling description for implementing an exemplary embodiment. It should be understood that various changes may be made in the function and arrangement of elements without departing from the spirit and scope of the invention as set forth in the appended claims.

Specific details are given in the following description to provide a thorough understanding of the embodiments. However, it will be understood by one of ordinary skill in the art that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in a figure. A process may correspond to a method, a function, a procedure, a subroutine, a subprogram, etc. When a process corresponds to a function, its termination can correspond to a return of the function to the calling function or the main function.

The term "computer-readable medium" includes, but is not limited to, portable or non-portable storage devices, optical storage devices, and various other mediums capable of storing, containing, or carrying instruction(s) and/or data. A computer-readable medium may include a non-transitory medium in which data can be stored and that does not include carrier waves and/or transitory electronic signals propagating wirelessly or over wired connections. Examples of a non-transitory medium may include, but are not limited to, a magnetic disk or tape, optical storage media such as compact disk (CD) or digital versatile disk (DVD), flash memory, memory or memory devices. A computer-readable medium may have stored thereon code and/or machine-executable instructions that may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, or the like.

Furthermore, embodiments may be implemented by hardware, software, firmware, middleware, microcode, hardware description languages, or any combination thereof. When implemented in software, firmware, middleware or microcode, the program code or code segments to perform the necessary tasks (e.g., a computer-program product) may be stored in a computer-readable or machine-readable medium. A processor(s) may perform the necessary tasks.

FIG. 1 illustrates a system 100 for distributing EMRs (electronic medical records), requests to generate medical imaging reports, and medical imaging reports that include medical imaging. System 100 includes medical imaging devices. The medical imaging devices may include, but are not limited to, X-ray device 105, MRI device 110, and CT scan device 115.

Other types of medical imaging devices (not shown) include ultrasound devices, endoscopy devices, elastography devices, tactile imaging devices, thermography devices, medical photography devices, nuclear medicine functional imaging devices (e.g., positron emission tomography (PET) devices, single-photo emission computed tomography (SPECT) devices, etc.), and/or the like. System 100 also includes care system 153, imaging selection device 133, distribution device 190, and radiology terminals 171, 172, and 173.

In the illustrated embodiment, X-ray device 105 is networked to care system 153 via link 143. Similarly, MRI device 110 is networked to care system 153 via link 145 and CT scan device 115 is networked to care system 153 via link 147. Links 143, 145, 147 may include Ethernet connections, wireless connections, or any other suitable network and/or networking protocol. For example, links 143, 145, 147 may be implemented as part of a personal area network (PAN), a local area network (LAN), a metropolitan area network (MAN), a wide area network (WAN), a storage area network (SAN), an enterprise private network (EPN), a virtual private network (VPN), and/or the like. Links 143, 145, 147 may represent communication via any suitable network protocol, such as WiFi/WiMAX, Bluetooth, fibre channel network protocols, TCP/IP, OSI, SSH, SMB, FTP, SMTP, HTTP, HTTPs, SSL, SFTP, and/or the like.

Care system 153 may include a networked datastore suitable to store EMRs, medical imaging, patient information, and the like, such as network-attached storage (NAS) or the like. Care system 153 may include, for example, EMR storage, a Picture Archiving and Communication System (PACS), a Radiology Information System (RIS), and/or the like, as discussed further herein. In some embodiments, care system 153 is a data storage server connected to a network that provides access to EMRs and other records by clients, such as medical facilities, doctors, patients, caregivers, and/or radiologists. Care system 153 may provide access to EMRs and other records using network file sharing protocols such as Network File System (NFS) protocol, Server Message Block (SMB)/Common Internet File System (CIFS) protocol, Apple Filing Protocol (AFP), combinations thereof, and/or the like. Care system 153 may include redundant memory backups to ensure the integrity of the EMRs. The networked datastore may have Terabytes of storage, for example. Care system 153 may include, for example, primary storage, secondary storage, tertiary storage, and/or offline storage. Care system 153 may further include processors, in some embodiments.

Imaging selection device 133 is configured to access care system 153 and medical imaging stored in care system 153. Imaging selection device 133 is configured to read EMRs stored in care system 153 as well as write to EMRs stored in care system 153 via link 149. Link 149 may include Ethernet connections, wireless connections, or other suitable networking protocol that facilitates read and/or write access to the particular care system 153.

X-ray device 105, MRI device 110, CT scan device 115, care system 153, and imaging selection device 133 may all be included in a same medical facility such as a hospital or clinic. Alternatively, the medical imaging devices may be in use at more than one clinic while care system 153 is not co-located at the same physical site of the medical imaging devices. In other words, care system 153 may be located locally or remotely with respect to a medical facility. It is contemplated that more than one care system 153 may be implemented in some embodiments.

Imaging selection device 133 is configured to access medical imaging files within care system 153 as well as certain medical data that is germane to analyzing medical imaging. Some medical data that is included in EMRs stored in care system 153 is not germane to medical imaging files. For example, a patient's social security number is not necessarily useful in analyzing medical imaging. Imaging selection device 133 sends medical imaging files and other relevant medical data that is relevant to analyzing medical imaging to distribution device 190, via link 163. Distribution device 190 may be a cloud server physically located at a datacenter in some embodiments. System 100 may include more than one distribution device 190 that are stored in different regional locales, for example. Imaging selection device 133 may access the distribution device 190 that is within closest physical proximity to the imaging selection device 133 in some embodiments. In some embodiments, imaging selection device 133 may select a distribution device 190 according to some other criteria, such as network traffic at particular distribution devices 190.

In some embodiments, imaging selection device 133 may generate a request (also referred to herein as an "order") for a medical imaging report (also referred to herein as a "report file"). The medical imaging report may include at least one image file (also referred to herein as "medical imaging") and metadata. The metadata may include descriptors of the image file, the request, and/or the medical imaging report, such as user data (e.g., data associated with the patient, such as a patient name, a patient date of birth, a patient identifier, etc.), site data (e.g., data associated with the body site that is imaged in the image file), and modality data (e.g., data associated with the medical imaging device used to create the image file).

In some embodiments, distribution device 190 receives the medical images and other relevant medical data and instead generates the request for a medical imaging report. The request is assigned to a radiologist and then transferred to the device/system (e.g. 171, 172, or 173) used by the assigned radiologist via one of network links 193. The server may assign the task to a certain radiologist based on radiology specialty (e.g., neurology, oncology, etc.), radiologist availability, a number of tasks already in a radiologist queue, or a variety of other factors.

In either embodiment, the assigned radiologist will generate a report based on viewing the medical images and corresponding relevant medical data and send the report back to distribution device 190, via link 193. Distribution device 190 transmits the report back to imaging selection device 133. The report may be in a designated (e.g., standardized) format for efficient processing by imaging selection device 133. Imaging selection device 133 stores the report in care system 153 so that it is accessible for health care providers, facilities, caregivers, patients, etc., that may have access to care system 153.

Figure 2:
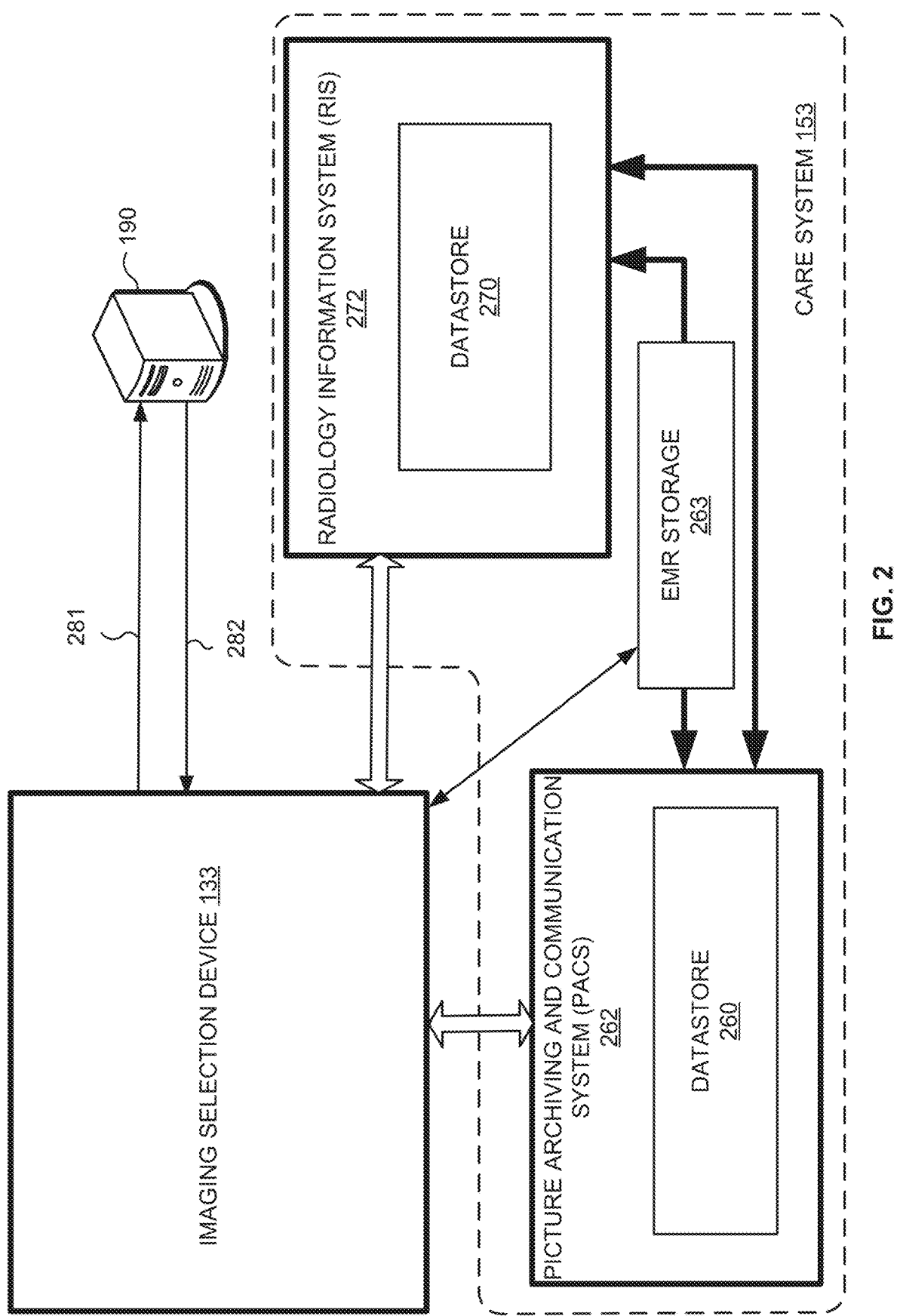
FIG. 2 is a system diagram illustrating a medical imaging report distribution system according to some embodiments of the invention.

FIG. 2 illustrates a system for distributing medical imaging records (e.g., medical images, EMRs, requests for medical imaging reports, medical imaging reports, etc.) that may include medical imaging. The system includes an exemplary imaging selection device 133 in communication with a distribution device 190 (also referred to herein as a "hub"). The system also includes care system 153. Care system 153 may include, for example, a Picture Archiving and Communication Systems (PACS), EMR storage 263, and/or a Radiology Information System (RIS) 272. As appreciated by one skilled in the art, one, none or multiple of each of these components may exist in care system 153. For example, there may be one RIS 272 per medical imaging device (e.g., X-ray device, MRI device, etc.) at a given medical imaging facility, one PACS 262 per medical imaging facility, and one remote EMR storage 263 located in the cloud.

In use, the imaging selection device 133 may receive medical imaging for a patient from a RIS 272 of a particular medical imaging device, and/or from PACS 262 of a particular medical imaging facility. The medical imaging may be stored in datastore 260 of PACS 262 and/or datastore 270 of RIS 272. In another example, the imaging selection device 133 may receive medical imaging for a patient as part of an EMR stored in EMR storage 263. In some embodiments, PACS 262 and RIS 272 may have access to one another by a link to augment the respective medical records utilizing data from the other system.

In response to receiving medical imaging for a patient, the imaging selection device 133 may request additional medical records from PACS 262, RIS 272, and/or EMR storage 263 that are relevant to the medical imaging to create a full study profile for the patient. The full study profile may include the initially received medical imaging and/or some or all of the additional medical records. For example, if the medical imaging received is for a left knee of a patient, the imaging selection device 133 may request all previous medical imaging made of the left knee of the patient in the patient's history, as well as any other relevant information (e.g., prior diagnoses, prior surgeries, prescribed medications, physical therapy records, etc.). The additional medical records may be retrieved by using one or more identifiers included in the initially received medical imaging, such as a patient's name, a patient's date of birth, a patient identification number, and/or the like. The imaging selection device 133 may then filter and format the study profile. The imaging selection device 133 may transmit the study profile 281 to the distribution device 190. The distribution device 190 may receive the study profile 281 and append it to a request for a medical imaging report. In other words, the request may include the study profile 281.

In some embodiments, the imaging selection device 133 may instead forward the medical imaging for a patient to the distribution device 190. The distribution device 190 may request additional medical records from the imaging selection device 133, which may in turn request the additional medical records from PACS 262, RIS 272, and/or EMR storage 263 that are relevant to the medical imaging to create a full study profile for the patient. The full study profile may include the initially received medical imaging and/or some or all of the additional medical records (e.g., additional medical imaging). For example, if the medical imaging received is for a left knee of a patient, the imaging selection device 133 may request all previous medical imaging made of the left knee of the patient in the patient's history, as well as any other relevant information (e.g., prior diagnoses, prior surgeries, prescribed medications, physical therapy records, etc.). The additional medical records may be retrieved by using one or more identifiers included in the initially received medical imaging, such as a patient's name, a patient's date of birth, a patient identification number, and/or the like. The distribution device 190 may then filter and format the study profile. The distribution device 190 may append the study profile 281 to a request for a medical imaging report and transmit the request to a radiologist computer. In other words, the request may include the study profile 281.

The request may be assigned to a radiologist and then transferred to the device (e.g., 171, 172, and/or 173) used by the assigned radiologist via one of network links 193, as shown in FIG. 1. The assigned radiologist may generate a report file based on viewing the medical images included in the request and send a report file 282 back to distribution device 190. Distribution device 190 may transmit report file 282 back to imaging selection device 133. Report file 282 may include an identifier that identifies the patient or file that the imaging package originates from (e.g., a patient or record identification number, a patient name, a patient date of birth, and/or the like). The report file 282 may be in a designated format for efficient processing by imaging selection device 233, such as a standardized format. The report file 282 may be translated into a storing format that can be written back to the care system 153. Writing the translated report to the care system 153 may include accessing the identifier so that the correct patient's EMR can be updated with the report from the radiologist. The identifier may be any combination of letters, numbers, graphics, and/or symbols.

Imaging selection device 133, the components of care system 153, and/or distribution device 190 may use any suitable number of subsystems to facilitate the functions described herein. Such subsystems or components may be interconnected via a system bus. Subsystems may include a printer, keyboard, fixed disk (or other memory comprising computer readable media), display, which may be coupled to a display adapter, and others. Peripherals and input/output (I/O) devices, which may couple to an I/O controller, can be connected to the imaging selection device 133, the components of care system 153, and/or medical imaging distribution device 190 by any number of means. For example, an external interface can be used to connect the imaging selection device 133, the components of care system 153, and/or distribution device 190 to a WAN such as the Internet, input device, or a scanner. The interconnection via the system bus may allow the central processor to communicate with each subsystem and to control the execution of instructions from system memory or the fixed disk, as well as the exchange of information between subsystems. The system memory and/or the fixed disk may embody a computer-readable medium.

The functions of imaging selection device 133, the components of care system 153, and/or distribution device 190 described herein may be implemented as software code to be executed by a processor using any suitable computer language such as, for example, Java, C++, or Perl, using, for example, conventional or object-oriented techniques. The software code may be stored as a series of instructions or commands on a computer-readable medium, such as a random access memory (RAM), a read only memory (ROM), a magnetic medium such as a hard drive or a floppy disk, and/or an optical medium such as a CD-ROM. The computer readable medium may be any combination of such storage or transmission devices.

Such programs may also be encoded and transmitted using carrier signals adapted for transmission via wired, optical and/or wireless networks conforming to a variety of protocols, including the Internet. As such, a computer-readable medium according to an embodiment of the present invention may be created using a data signal encoded with such programs. Computer-readable media encoded with the program code may be packaged with a compatible device or provided separately from other devices (e.g., via Internet download). Any such computer-readable medium may reside on or within a single computer product (e.g., a hard drive a CD, or an entire computer system), and may be present on or within different computer products within a system or network. The systems may include a display for providing any of the results described herein to a user.

Figure 3:
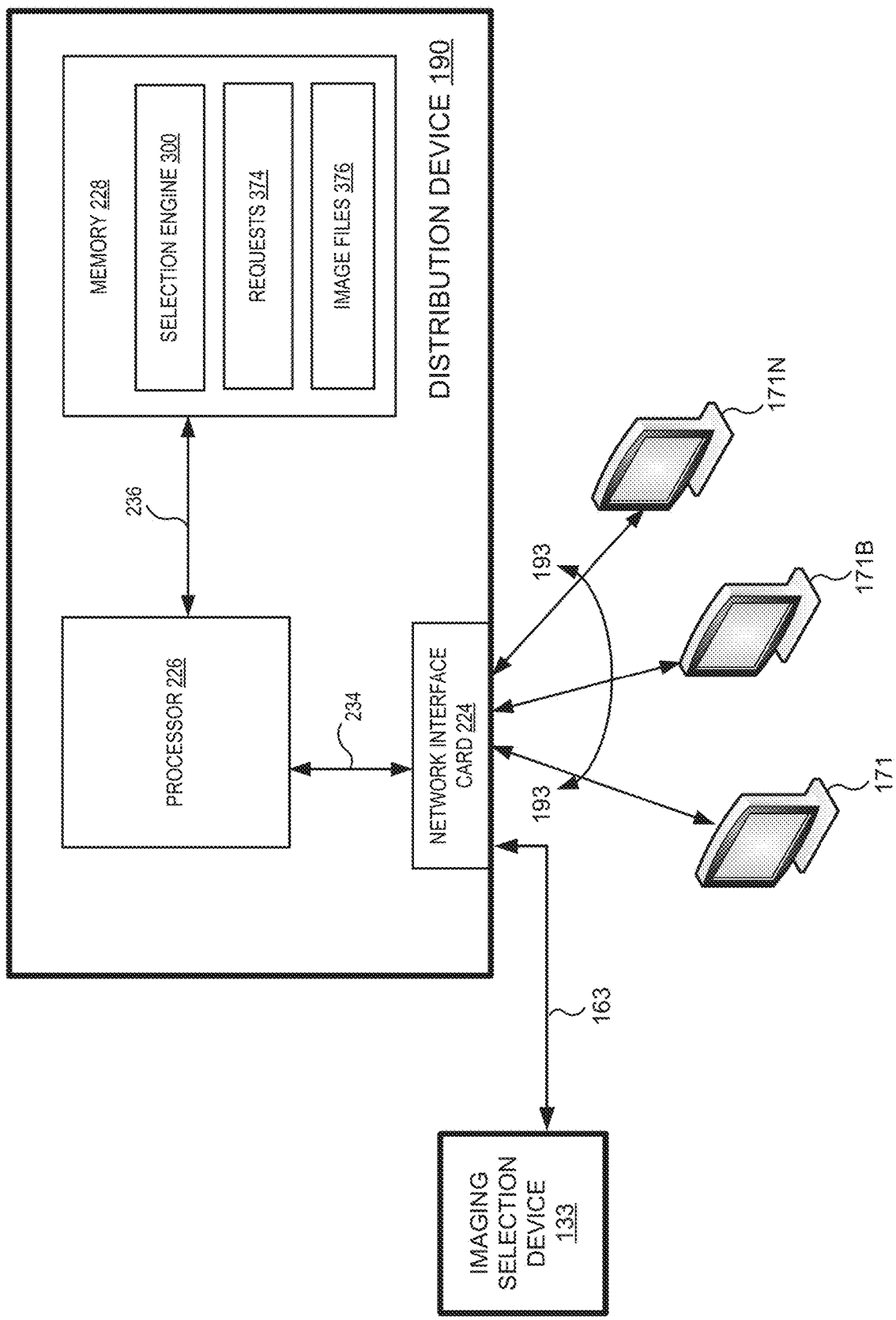
FIG. 3 is a system diagram illustrating a distribution device according to some embodiments of the invention.

FIG. 3 is a system diagram illustrating the details of a distribution device 190 according to some embodiments of the invention. Distribution device 190 may be communicatively coupled to imaging selection device 133 via link 163 and a plurality of radiologist computers 171A, 171B, 171N via links 193. Although shown and described as being coupled to three radiologist computers 171A, 171B, 171N, it is contemplated that distribution device 190 may be coupled to any number of radiologist computers.

Distribution device 190 may include memory 228 (e.g., a computer-readable medium) that includes a selection engine 300, requests 374, and image files 376. The selection engine 300, requests 374, and/or image files 376 may be stored in one or more volatile or nonvolatile datastores associated with the distribution device 190. These datastores may be internal or external to the distribution device 190. Distribution device 190 may also include a processor 226. The processor 226 may include a microprocessor, FPGA, or any other suitable logic device. The processor 226 may interface with the memory 228 over a PCI (Peripheral Component Interface) bus 236, for example.

Distribution device 190 may also include a network interface card 224 or any other suitable networking hardware (e.g., an Ethernet card or 802.11 WiFi card) to interface with the imaging selection device 133 and the radiologist computers 171A, 171B, 171N. The network interface card 224 may interface with the processor 226 over a PCI (Peripheral Component Interface) bus 234, for example. The network interface card 224 may interface with imaging selection device 133 to access medical imaging records (e.g., EMRs, medical imaging, requests for medical imaging reports, other medical records, etc.) that are stored on one or more datastores of the imaging selection device 133. In some embodiments, the medical imaging may be compressed for transmission. The compression may be lossless compression, in one embodiment. Possible compression modes include JPLL (JPEG lossless), JLSL (JPEG-LS Lossless), J2KR (JPEG 2000 Lossless), and JPLY (JPEG Lossy). In some embodiments, the requests 374 for medical imaging reports received from the imaging selection device 133 may be stored in memory 228 of the distribution device 190. In addition, the medical imaging received from the imaging selection device 133 may be stored in memory 228 of the distribution device 190 as image files 376.

Once the requests 374 for medical imaging reports are received, the requests 374 are processed by the selection engine 300. The selection engine 300 may be configured to, in conjunction with the processor 226, extract metadata from the requests 374, including user data, site data, and modality data. The selection engine 300 may use the metadata to retrieve and filter one or more supplemental image files related to the patient that is the subject of the request, as discussed further herein. The selection engine 300 may append the one or more supplemental image files to the request 374 and forward the request 374 to a radiologist computer 171A, 171B, 171N. The radiologists may use the radiologist computers 171A, 171B, 171N to generate report files (also referred to herein as "medical imaging reports"). The radiologist computers 171A, 171B, 171N may transmit the report files back to the distribution device 190 via links 193. In some embodiments, the report files may be stored in memory 228 of the distribution device 190 (not shown). The report files may be routed back to the appropriate imaging selection device 133 that initiated the request for a particular report file.

When received by the imaging selection device 133, the imaging selection device 133 may translate the report file into a storing format that can be written back to the care system (not shown) (e.g., PACS, EMR storage, and/or RIS) of the particular medical facility that took the medical imaging. The translated report file may then be written to the care system. Writing the translated report to the care system may include accessing one or more patient identifier so that the correct patient's EMR can be updated with the report file from the radiologist.

Figure 4:
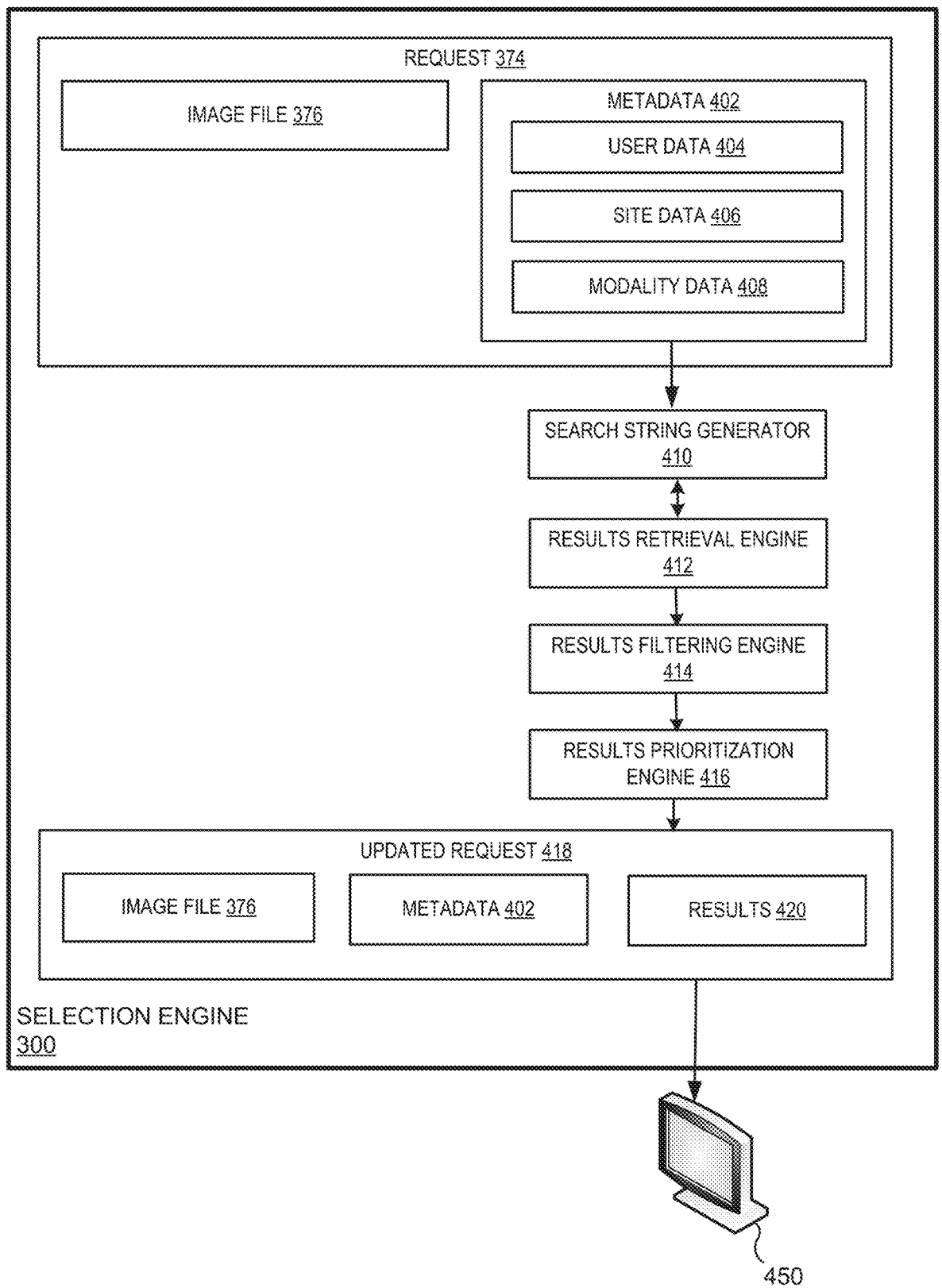
FIG. 4 is a system diagram illustrating a selection engine of a distribution device according to some embodiments of the invention.

FIG. 4 is a system diagram illustrating a selection engine 300 of a distribution device according to some embodiments of the invention. Selection engine 300 may be configured to select and transmit one or more supplemental image files related to medical imaging received from an imaging selection device based on metadata. In selection engine 300, a request 374 for a medical imaging report is received. The request 374 may be received from a separate device on the network, such as an imaging selection device, for example. The imaging selection device may store a plurality of image files, including the at least one image file 376 included in the request 374. The request 374 may be stored in memory of the distribution device. The request 374 may include at least one image file 376 and metadata 402. The metadata 402 may include user data 404, site data 406, and modality data 408. The user data 404 may include any data associated with the patient imaged in the image file 376, such as a name, a date of birth, a patient identifier (e.g., a social security number, an anonymized patient number, etc.), combinations thereof, and/or the like. The site data 406 may include any data associated with the site of the patient's body shown in the image file 376 (e.g., left knee, right ankle, chest, abdomen, head, neck, right shoulder, left hand, etc.). The modality data 408 may include any data associated with the medical imaging device used to generate the image file 376 (e.g., a type of medical imaging device, such as X-ray, CT scan, ultrasound, etc., a model of medical imaging device, a year of manufacture of the medical imaging device, a manufacturer of the medical imaging device, etc.).

The request 374 may be fed into a search string generator 410. The search string generator 410 may be configured to extract the metadata from the request. The search string generator 410 may further be configured to generate a search string for at least one supplemental image file of the patient based on the user data 404. For example, the search string generator 410 may generate a search string for medical imaging stored in association with a name of "DOE, JOHN" with a birthdate of "1957-06-30". The search string generator 410 may be configured to provide the search string to the results retrieval engine 412.

In some embodiments, the results retrieval engine 412 may be configured to transmit the search string to the imaging selection device (or other device from which the request 374 was received). In some embodiments, the results retrieval engine 412 may be configured to transmit the search string to a third party device (i.e., a device separate from that which transmitted the request 374) that has access to a plurality of image files. The imaging selection device (or third party device) may receive the search string and execute the search string on the plurality of files stored thereon or accessible thereby to generate a set of results responsive to the search string. For example, for a search string of a name of "DOE, JOHN" with a birthdate of "1957-06-30", all image files for a John Doe with a birthdate of Jun. 30, 1957 may be retrieved. The imaging selection device (or third party device) may transmit the set of results responsive to the search string (including the retrieved image files) to the results retrieval engine 412 (via a processor and network interface card, for example). The results retrieval engine 412 may be configured to transmit the set of results to the results filtering engine 414.

The results filtering engine 414 may be configured to filter the set of results using the site data 406 to generate a subset of results. In the above example, the results filtering engine 414 may receive all image files for a John Doe with a birthdate of Jun. 30, 1957. Many of these image files may not be relevant to the image file 376 received in the request 374. Therefore, the results filtering engine 414 may filter the results for image files having the same or similar site data 406. For example, if the site data 406 for John Doe is "left ankle", the results filtering engine 414 may filter the results for image files only related to the left ankle. In some embodiments, the results filtering engine 414 may also filter the results for image files showing sites proximate to the site data 406. For example, if the site data 406 for John Doe is "left ankle", the results filtering engine 414 may filter the results for images files both related to the left ankle and related to sites proximate to the left ankle (e.g., left foot, left shin, etc.). The proximity of various sites to each other may be predefined and stored by the distribution device for access by the results filtering engine 414. The results filtering engine 414 may be configured to transmit the subset of results (i.e., the filtered set of results) to the results prioritization engine 416.

The results prioritization engine 416 may be configured to prioritize the subset of results received from the results filtering engine 414 based on the modality data 408. In the above example, the results prioritization engine 416 may receive all image files showing the left ankle and left foot of a John Doe with a birthdate of Jun. 30, 1957. Some of these image files may be more relevant to the image file 376 received in the request 374, and/or more helpful to a radiologist generating a report file. Therefore, the results prioritization engine 416 may prioritize the results according to similarity of modality data 408. For example, if the modality data 408 includes "type: X-ray", "manufacturer: Medical Imaging Device Company", "year of manufacture: 2009", the results prioritization engine 416 may prioritize results based on similarities to this information. For example, the results prioritization engine 416 may prioritize a result having the same type and manufacturer first, a result having the same type but different manufacturer second, and a result having a different type third. In some embodiments, the results prioritization engine 416 may additionally or alternatively prioritize results using other criteria, such as the date that the medical imaging was generated (e.g., with the most recent relevant results first). In some embodiments, the results prioritization engine 416 may limit the number of results included in the prioritized subset of results to a top number of results (e.g., five most relevant results, top 20% of the most relevant results, etc.).

The results prioritization engine 416 may append the prioritized subset of results to the at least one image file in the request. Thus, the results prioritization engine 416 may generate an updated request 418 that includes the image file 376, the metadata 402, and the prioritized subset of results 420 (including the supplemental image files). The updated request 418 may be transmitted to a radiologist computer 450 external to the distribution device over the network. Radiologist computer 450 may be used to implement any of radiologist computers 171A, 171B, and/or 171N. The radiologist computer 450 may review the updated request 418, including the image file 376 and the metadata 402. Further, the radiologist computer 450 may review the supplemental image files in the subset of results 420 quickly and efficiently as needed, as they have already been transmitted to and downloaded at the radiologist computer 450. Thus, the radiologist computer 450 need not request the most relevant supplemental image files from the distribution device, which in turn would have to request them from the imaging selection device, causing delays. In some embodiments, metadata relating to all results corresponding to the user data retrieved by the results retrieval engine 412, filtered by the results filtering engine 414, and/or prioritized by the results prioritization engine 416 may be provided to the radiologist computer 450 in the results 420 (without their accompanying image files) to allow the radiologist computer 450 to view a description of and request image files for any of the results. However, those results outside of the prioritized subset of results 420 may take longer to download to the radiologist computer 450 if requested, as they have not been pre-cached onto the radiologist computer 450. After the radiologist computer 450 has reviewed the updated request 418, the radiologist computer 450 may generate a report file including at least the image file 376 and at least one medical notation analyzing the image file 376.

Figure 5:
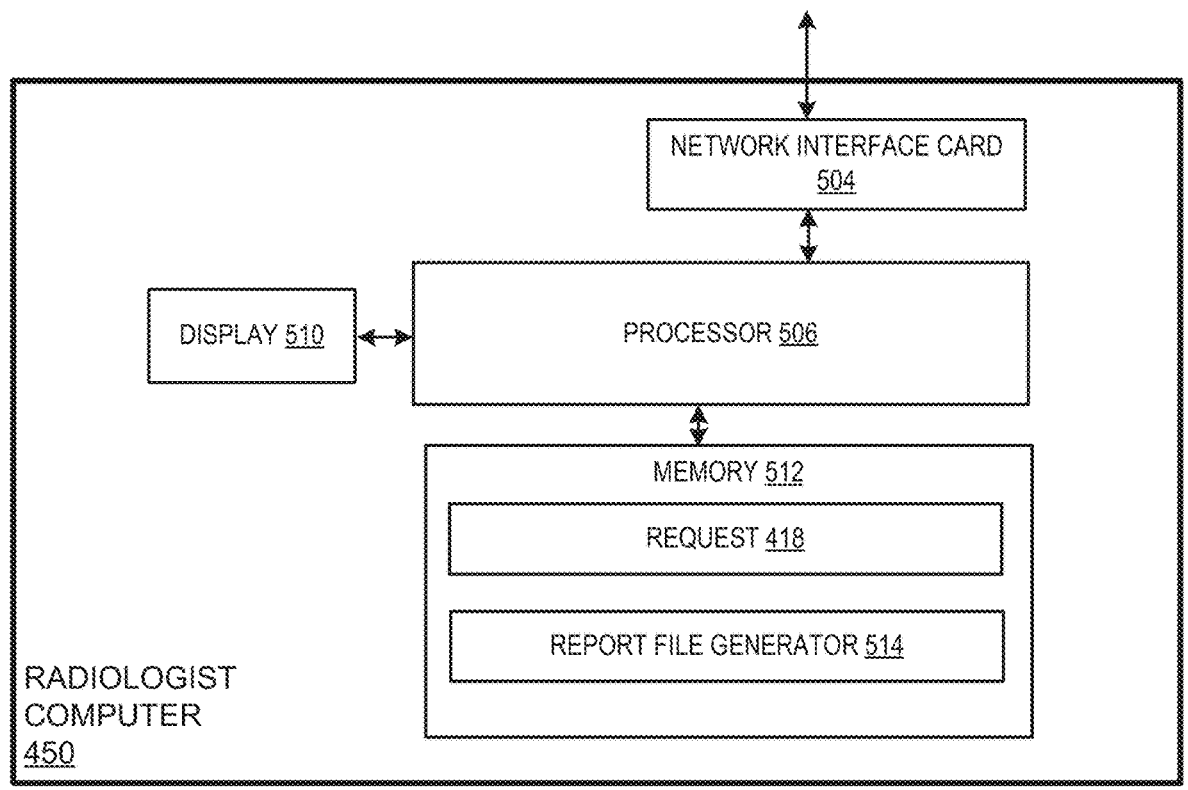
FIG. 5 is a system diagram illustrating a radiologist computer according to some embodiments of the invention.

FIG. 5 is a system diagram illustrating a radiologist computer 450 according to some embodiments of the invention. Radiologist computer 450 may be used to implement any of radiologist computers 171A, 171B, and/or 171N. Radiologist computer 450 may include a network interface card 504, a processor 506, a display 510, and a memory 512. The network interface card 504 may be used to receive requests from and/or transmit report files to the distribution device and/or any other systems described herein.

The processor 506 may be a processor, a microprocessor, an FPGA, or any other suitable logical device. Memory 512 may be a computer-readable medium and may be volatile or nonvolatile. Memory 512 may store a request 418 received by the radiologist computer 450 via the network interface card 504. The request 418 may be displayed on the display 510 of the radiologist computer 450. Memory 512 may further store a report file generator 514. The report file generator 514 may be used to generate report files based on the request 418. The report file generator 418 may be implemented in a browser (e.g., Google Chrome) executing entirely in the application layer of a protocol stack used to communicate with any of the systems described herein. The browser may execute any of the processes described herein to allow radiologists to receive and review requests 418 and complete and transmit report files in a zero footprint system, such that only a browser as an application and, in some embodiments, a corresponding extension, as required to execute the disclosed processes. In implementations that include a zero footprint system, any of the records and/or data described herein may be stored in a memory of a server, for example. The browser may then access this content stored in the memory of the server.

Figure 6:
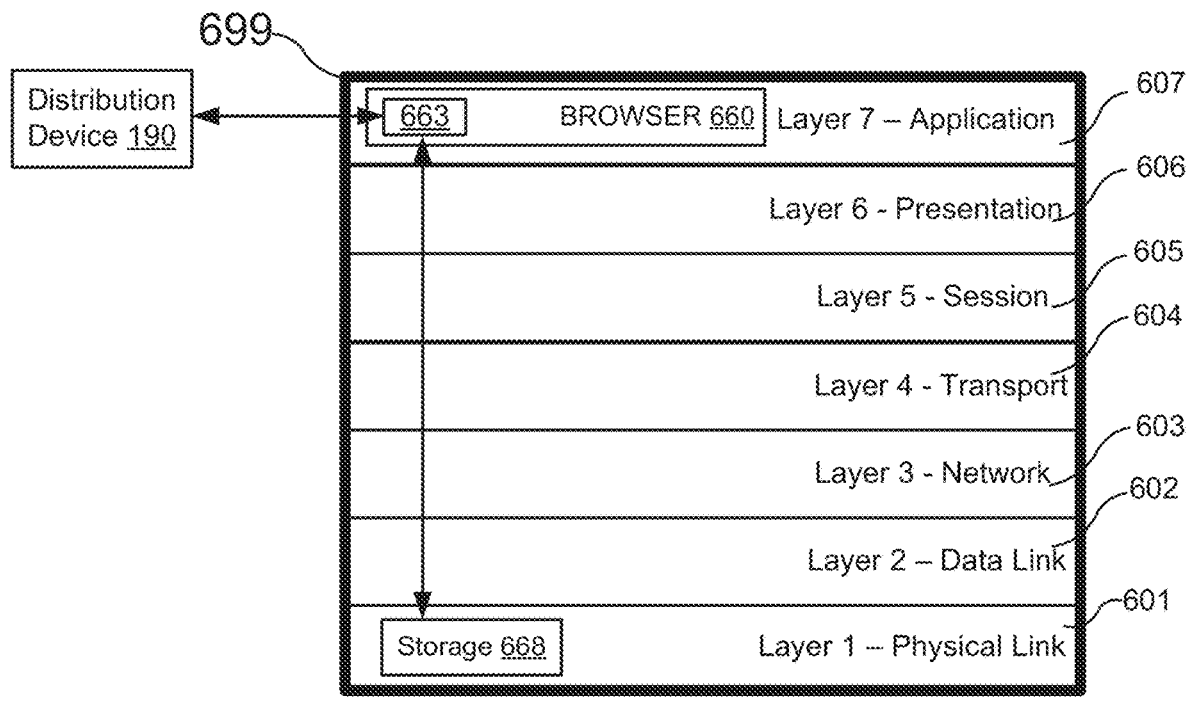
FIG. 6 is an architectural diagram illustrating the functional layers of a radiologist computer according to some embodiments of the invention.

FIG. 6 is a block diagram of a protocol stack 699 that may be implemented by the radiologist computer 450 in accordance with some embodiments. The radiologist computer 450 may implement the protocol stack to communicate with any of the other systems described herein, such as the distribution device 190. The protocol stack 699 may include one or more of seven layers: an application layer 607, a presentation layer 606, a session layer 605, a transport layer 604, a network layer 603, a data link layer 602, and a physical link layer 601. Together, these seven layers may represent a model, such as an Open Systems Interconnection (OSI) model. The OSI model of FIG. 6 may characterize the communication functions of the described systems. Although shown and described as having seven layers, it is contemplated that the protocol stack 699 may include more or fewer layers to perform less, the same, or additional functions.

According to the OSI model, the application layer 607 may interact with a user (e.g., via receiving user inputs and presenting outputs) and software applications implementing a communication component. The application layer 607 may synchronize communication between systems and determine resource availability. The application layer 607 may be application-specific, in that the specific functions dependent on the particular application being executed by the computing device.

For example, the application layer 607 may execute a browser 660 (e.g., Google Chrome) which in turn may execute the processes (e.g., of flowchart 900) of the disclosure with the assistance of an extension 663. Browser 660 and extension 663 may be executed entirely at the application layer 607. This allows for radiologists to receive and view medical imaging records (e.g., from EMR storage, PACS, and/or RIS 272 (not shown)), and complete and transmit report files in a zero footprint system in that only a browser as an application and corresponding extension are required to execute the disclosed processes. In implementations that include a zero footprint system, any of the records and/or data described herein may be stored in a memory of a server, for example. The browser and corresponding extension may then access this content stored in the memory of the server.

The presentation layer 606 may translate between application and network formats. Various applications and networks may implement different syntaxes and semantics. Thus, the presentation layer 606 may transform data from the network into a form that the application accepts. The presentation layer 606 may also format and encrypt data from the application to be sent on a network.

The session layer 605 may control connections between the systems and other devices and/or servers, as described herein. The session layer 605 may establish the connections, manage the connections, and terminate the connections used to communicate between the devices.

The transport layer 604 may provide techniques for performing quality of service functions during transfers of data between devices. The transport layer 604 may provide error control. For example, the transport layer 404 may keep track of data being transmitted and transmit any communications that fail. In addition, the transport layer 604 may provide an acknowledgment of successful data transmission and send the next data to be transmitted in a synchronous fashion if no errors occurred.

The network layer 603 may provide the means of transferring the data to and from the systems over a network. The source node and destination node of the systems may each have an address which permits the other to transfer data to it by providing the address with the data. The network layer 603 may also perform routing functions that allow it to a determine a path between the source node and destination node, possibly through other nodes.

The data link layer 602 may define and provide the link between a directly and physically connected source node and destination node. The data link layer 602 may further detect and correct errors occurring at the physical link layer 601. In some embodiments, the data link layer 602 may include two sublayers: a media access control (MAC) layer that may control how devices in the network gain access to data and gain permission to transmit it, and a logical link control (LLC) layer that may identify network layer 603 protocols and encapsulate them.

The physical link layer 601 may include one or more storage devices 668. The storage devices 668 may, for example, cache study profiles, medical imaging, and reports for transmission, as described further herein. The physical link layer 601 may define the electrical and physical specifications of the data. The physical link layer 601 may provide a physical medium for storing unstructured raw data to be transmitted and received.

Figure 7:
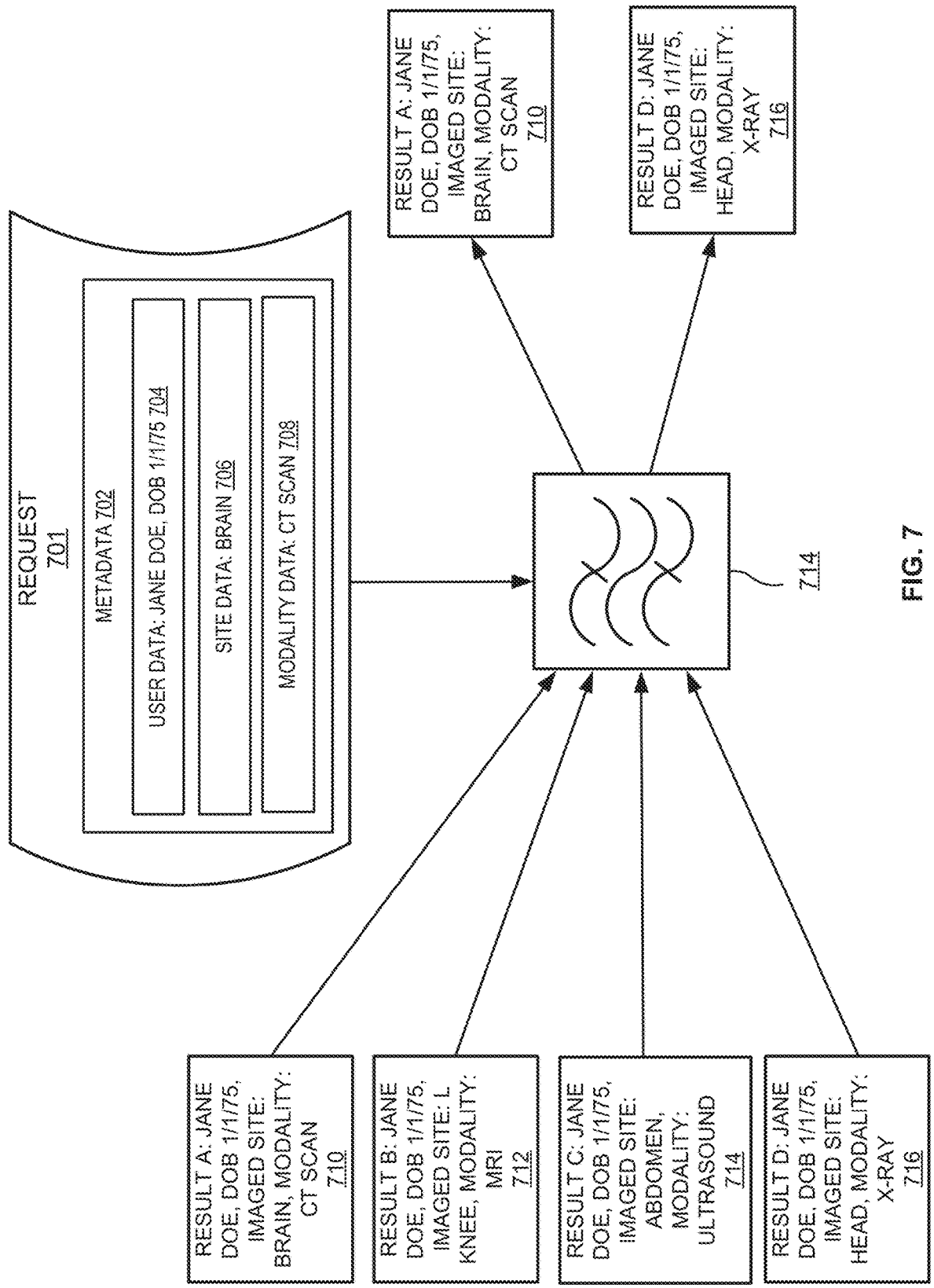
FIG. 7 is a system diagram illustrating a filter applied to image files according to some embodiments of the invention.

FIG. 7 is a system diagram illustrating a filter 714 applied to results of a medical imaging search for relevancy, according to some embodiments of the invention. Filter 714 may be implemented by the results filtering engine 414 of FIG. 4, for example. In the illustrated example, a set of results including results 710, 712, 714, 716 are input into the filter 714. Although illustrated and described as having four candidate results 710, 712, 714, 716, it is contemplated that any number of results may be input into filter 714.

Filter 714 may receive a request 701. The request 701 may include metadata 702, including user data 704, site data 706, and modality data 708. The metadata 702 may be similar to the metadata 402 of FIG. 4. In this example, the user data 704 may include a name ("JANE DOE") and a date of birth ("1/1/75"). The site data 706 may include a bodily location of the image ("brain"). The modality data 708 may include a type of medical imaging completed ("CT scan"). This metadata 702 may be applied by the filter 714 to generate a subset of results that are most relevant. In some embodiments, the filter 714 may not receive the full request 701, and may instead receive the metadata to be applied by the filter 714 (e.g., the site data 706).

For example, the filter 714 may receive four results as input: result A 710 (user data: Jane Doe, DOB 1/1/75; site: brain; modality: CT scan), result B 712 (user data: Jane Doe, DOB 1/1/75; site: left knee; modality: MRI), result C 714 (user data: Jane Doe, DOB: 1/1/75; site: abdomen; modality: ultrasound), and result D 716 (user data: Jane Doe, DOB 1/1/75; site: head, modality: X-ray). The results 710-716 may have been previously searched for from a plurality of image files relating to a plurality of users by a search string using the user data 704. The filter 714 may receive the results 710-716 and filter them using the site data 706, such that the results are further limited to those relevant to the site data 706. For example, the filter 714 may limit the results 710-716 to those results that are for the brain and are proximate to the brain. Thus, the filter 714 may return result A 710, which is of the brain, and result D 716, which is of the head.

Figure 8:
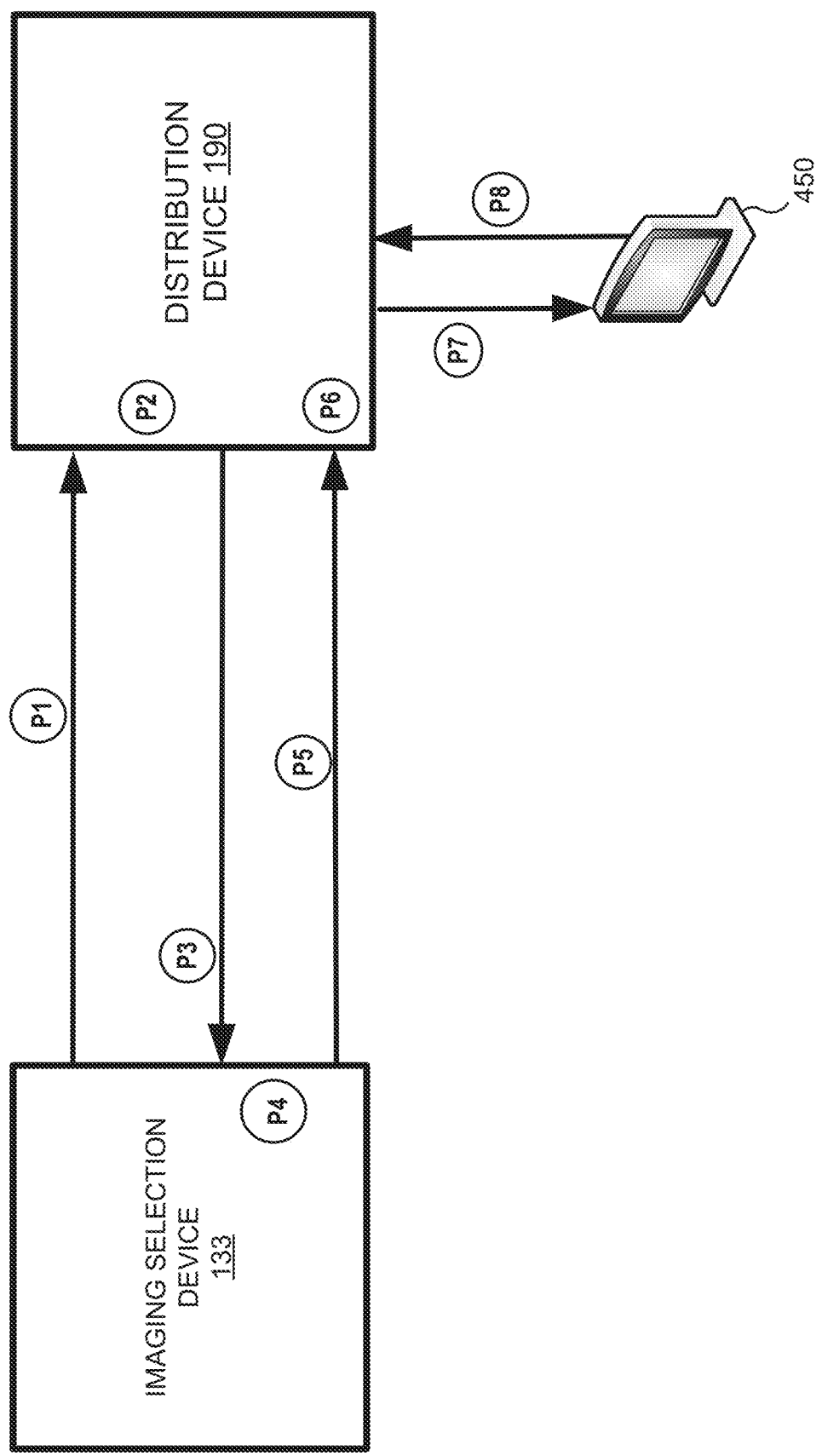
FIG. 8 is a hybrid diagram illustrating a system and method for pre-caching radiological imaging for distribution according to some embodiments of the invention.

FIG. 8 is a hybrid diagram illustrating a system and method for pre-caching radiological imaging for distribution according to some embodiments of the invention. FIG. 8 may include imaging selection device 133, distribution device 190, and radiologist computer 450. At process block P1, imaging selection device 133 may transmit a request for a report file to distribution device 190 over a network connection. The request may include one or more current image files. The one or more current images files may include the medical imaging that needs to be analyzed by a radiologist. The radiologist may generate a report file that describes his or her findings after viewing the one or more current image files. The one or more current images files may include, for example, an X-ray, a series of X-rays, an MRI, a CT scan, ultrasound images, bone scan images, and/or any other medical imaging generated by a medical imaging device.

The request may include metadata relating to the one or more current image files. The metadata may include user data. The user data may include the patient's name, birthdate, social security number, and/or identifier (e.g., medical records number), for example. The metadata may further include site data indicating a body part or region shown in the one or more current image files. For example, the site data may indicate an ankle, foot, toe, knee, pelvis, abdomen, shoulder, chest, hand, finger, wrist, elbow, head, neck, heart, brain, and/or the like. The metadata may further include modality data associated with the one or more current image files. For example, the modality data may indicate an X-ray, an MRI, a CT scan, an ultrasound, or any other medical imaging device.

When radiologists analyze current image files, they may also want to review other relevant medical imaging. For example, a brain MRI from six months ago may be relevant and therefore useful to view in analyzing a most recent brain MRI included in a current image file. Therefore, relevant image files that are related to current image files may be useful to provide to a radiologist using the radiologist computer 450. Relevant image files may include medical imaging that is of the same body part or region or a body part or region proximate to the body part or region shown in the current image files. As an example, imaging of the chest may be proximate to the shoulder and include at least a portion of the shoulder. Hence, image files of the chest may be useful in evaluating current image files related to the shoulder. Relevant image files may be further narrowed by modality data. For example, previous X-ray imaging of a knee may not be as useful in evaluating a current MRI of a knee, whereas a previous MRI would be more useful.

At process block P2, distribution device 190 receives the request and determines which supplemental image files should be fetched that are related to the current image files. For example, the request may be received by a network interface card of the distribution device 190. The distribution device 190 may parse or select user data from the request. The distribution device 190 may also determine site data of the current image files. The distribution device 190 may also determine modality data of the current image files.

Using one or more of the user data, the site data, and/or the modality data, distribution device 190 may generate a pre-fetching query to retrieve related image files from an EMR datastore via imaging selection device 133. Using the user data, distribution device 190 may construct a fuzzy search by generating approximate string matches from the user data. For example, if the patient's name is "John F. Smith", an approximate string match may include names such as "John Smith" or "Smith, John F.". Distribution device 190 may also generate proximate body sites that may be relevant to the site data of the current image files. For example, if the site data indicates a chest, proximate site data may include shoulders and the heart. Proximate site data may be returned in a proximate site functions executed by processing logic of the distribution device 190, for example. Similarly, modalities that would be useful in evaluating the current image files may also be determined by the distribution device 190.

At process block P3, a pre-fetch query may be transmitted to the imaging selection device 133 by the network interface card of the distribution device 190. The pre-fetch query may include a pre-fetch identifier and search elements. The search elements may include user data and approximate string matches of the user data; site data and proximate site data; and modality data and relevant modality data.

At process block P4, imaging selection device 133 may search datastores for relevant image files using one or more of the search elements. In some embodiments, imaging selection device 133 may search recent EMR datastores (e.g., last six months of imaging) that are co-located in a same medical facility as imaging selection device 133. In some embodiments, imaging selection device 133 may search a long-term EMR datastore (e.g., older than six months) that is remote from the imaging selection device 133.

At process block P5, imaging selection device 133 may transmit a pre-fetching response to distribution device 190 via a network connection. In the illustrated example, the pre-fetching response includes the pre-fetch identifier so that distribution device 190 can identify the pre-fetching response as responsive to the pre-fetch query. The pre-fetching response also includes related image files. The related image files include user data matching the user data of the current image files or approximate string matches of the user data of the current image files.

The related image files may include site data that matches the site data in the current image files or is proximate to site data in the current image files. The related image files may further include modality data that matches modality data of the current image files or is relevant to the modality data of the current image files. The pre-fetching response may include one or more set of related image files.

At process block P6, distribution device 190 may receive the related image files and pre-cache them in a memory of distribution device 190. With the current image files and the related image files pre-cached on distribution device 190, they will be easily accessed by a radiologist who wants to view them rather than waiting for distribution device 190 to request them from imaging selection device 133, which then must query additional datastores for the related image files and then transfer back the images files (which are often of significant size) to distribution device 190. In one example, the related image files are compared to the current image files in an image processing algorithm to ensure that related image files are of the same person as current image files.

At process block P7, distribution device 190 may link the one or more related image files with the current image files and package them as an updated request. The updated request may be transmitted by the network interface card of the distribution device 190 to the radiologist computer 450. The radiologist computer 450 is therefore able to pre-cache the current image files and the related image files locally so that when a radiologist wants to view the related image files, they are available without a time lag associated with fetching those related image files from datastores via distribution device 190 and imaging selection device 133. In one example, the related image files are ranked in order of relevance and the most relevant related imaging set is transmitted in the updated request before lesser relevant related image files. Related image files of the same body part, using the same modality, and most recent to the current image files may be ranked as the most relevant related image files, for example, and transmitted to the radiologist computer 450 prior to a lesser relevant related imaging file in the updated request.

In some embodiments, the updated request is sent to the radiologist computer 450 at a time subsequent to the radiologist selecting a software button on a browser interface that transmits an active status alert to distribution device 190 that indicates that a radiologist is active reading medical imaging. The browser interface may be specifically configured to view, analyze, and generate medical imaging reports and be running on an operating system of the radiologist computer 450. After a radiologist "reads" the current image files (and may view related image files in the analysis), the radiologist may generate a report file that is transmitted back to distribution device 190 via a network connection in process block P8. Distribution device 190 may then transmit the report file back to imaging selection device 133 or otherwise forward the report file on to the facility or medical professional that is caring for the patient who is the subject of the current image files.

In one example, distribution device 190 may compress the related image files and send compressed versions of the related image files to the radiologist computer 450. If a radiologist would like to view a an uncompressed version of a particular related image file, the radiologist may select a software button in the browser interface to request that the uncompressed version of the related image files be sent to radiologist computer 450. When distribution device 190 receives this request, distribution device 190 sends the radiologist computer 450 the uncompressed version of the related image files for viewing by the radiologist. In one example, distribution device 190 may only compress the related image files if the measured download speed of the radiologist computer 450 (measured by a module of the processor of radiologist computer 450) is measured to be below a certain speed (e.g. 10 Megabytes/second). Radiologist computer 450 may communicate its download speed to distribution device 190 via a network connection, for example.

Figure 9:
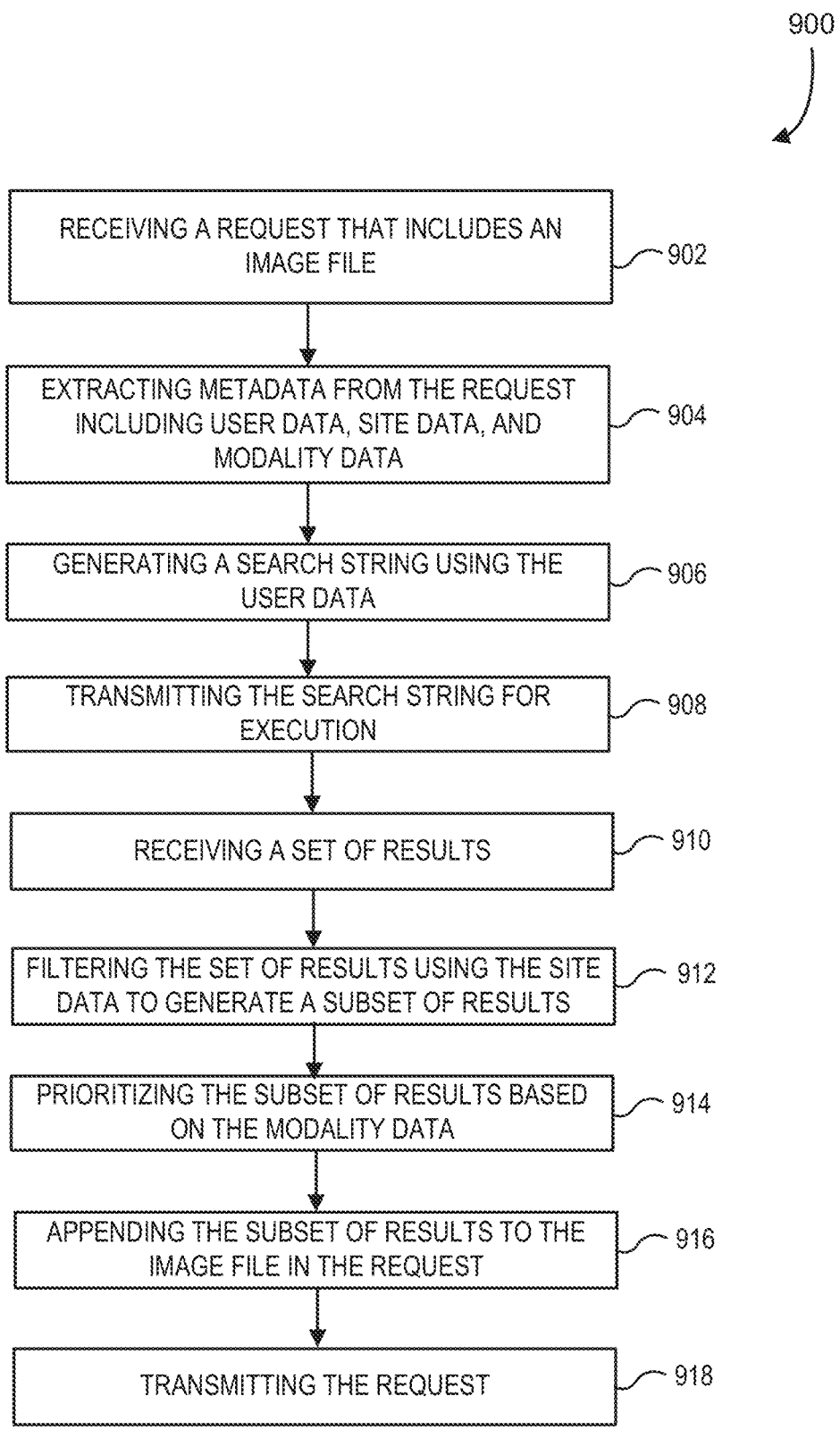
FIG. 9 is a flow chart illustrating a method for pre-caching radiological imaging for distribution according to some embodiments of the invention.

FIG. 9 is a flow chart 900 illustrating a method for pre-caching radiological imaging for distribution according to some embodiments of the invention. The process is illustrated as a logical flow diagram, each operation of which represents a sequence of operations that can be implemented in either hardware, computer instructions, or a combination thereof. In the context of computer instructions, the operations represent computer-executable instructions stored on one or more computer-readable storage media that, when executed by one or more processors, perform the recited operations. Generally, computer-executable instructions include routines, programs, objects, components, data structures, and the like that perform particular functions or implement particular data types. The order in which the operations are described is not intended to be construed as a limitation, and any number of the described operations can be omitted or combined in any order and/or in parallel to implement this process and any other processes described herein.

Some or all of the process (or any other processes described herein, or variations and/or combinations thereof) may be performed under the control of one or more computer systems configured with executable instructions and may be implemented as code (e.g., executable instructions, one or more computer programs or one or more applications). Network hardware and processing logic of distribution device 190 may execute the process blocks show in process 900, for example. The code may be stored on a computer-readable storage medium, for example, in the form of a computer program including a plurality of instructions executable by one or more processors. The computer-readable storage medium may be non-transitory.

At process block 902, a request to generate a report file is received by a network interface of a server (e.g., a distribution device) in a network. The request may include at least one image file. The at least one image file may depict a site of the user. The at least one image file may have been generated by an imaging device. The request may be received from a first node external to the server in the network (e.g., an imaging selection device). The first node may store a plurality of image files including the at least one image file received in the request.

At process block 904, metadata may be extracted from the request. The metadata may include user data, site data, and modality data. The user data may be data that is associated with the user shown in the at least one image file. The site data may be data that is associated with the site of the user depicted in the at least one image file. The modality data may be data that is associated with the imaging device used to generate the at least one image file.

At process block 906, a search string may be generated for at least one supplemental image file of the user based on the user data. At process block 908, the search string may be transmitted to the first node for execution on the plurality of image files. For example, the plurality of image files stored by the first node may be searched for all image files associated with a particular name and date of birth. At process block 910, a set of results responsive to the search string may be received from the first node. The set of results may include the at least one supplemental image file of the user.

At process block 912, the set of results may be filtered using the site data to generate a subset of results. For example, the set of results may return all image files associated with a particular name and date of birth. These image files may be filtered to select only those image files that are of the same site as the original image file or a site proximate to the site indicated by the original image file.

At process block 914, the subset of results may be prioritized based on the modality data. For example, the subset of results may return all image files associated with a particular name and date of birth that are of a certain site or proximate to that site. However, some of those results may be less relevant to the original image file due to their modality. Thus, the subset of results may be prioritized with the image files having the same modality first, a similar modality second, and other modalities third.

At process block 916, the prioritized subset of results may be appended to the at least one image file in the request. For example, the supplemental image files corresponding to the subset of results may be attached to the request in prioritized order after the original image file. At process block 918, the request may be transmitted to a second node external to the server in the network (e.g., a radiologist computer). The request may include the at least one image file and the prioritized subset of results. In some embodiments, the request may include a listing of all of the results associated with the user data, with only the corresponding supplemental image files being included for the prioritized subset. The supplemental image files associated with the other results (i.e., not included in the prioritized subset) may be manually requested for download.

As noted, the computer-readable medium may include transient media, such as a wireless broadcast or wired network transmission, or storage media (that is, non-transitory storage media), such as a hard disk, flash drive, compact disc, digital video disc, Blu-ray disc, or other computer-readable media. The computer-readable medium may be understood to include one or more computer-readable media of various forms, in various examples.

In the foregoing description, aspects of the application are described with reference to specific embodiments thereof, but those skilled in the art will recognize that the invention is not limited thereto. Thus, while illustrative embodiments of the application have been described in detail herein, it is to be understood that the inventive concepts may be otherwise variously embodied and employed, and that the appended claims are intended to be construed to include such variations, except as limited by the prior art. Various features and aspects of the above-described invention may be used individually or jointly. Further, embodiments can be utilized in any number of environments and applications beyond those described herein without departing from the broader spirit and scope of the specification. The specification and drawings are, accordingly, to be regarded as illustrative rather than restrictive. For the purposes of illustration, methods were described in a particular order. It should be appreciated that in alternate embodiments, the methods may be performed in a different order than that described.

Where components are described as performing or being "configured to" perform certain operations, such configuration can be accomplished, for example, by designing electronic circuits or other hardware to perform the operation, by programming programmable electronic circuits (e.g., microprocessors, or other suitable electronic circuits) to perform the operation, or any combination thereof.

The various illustrative logical blocks, modules, circuits, and algorithm steps described in connection with the embodiments disclosed herein may be implemented as electronic hardware, computer software, firmware, or combinations thereof. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The techniques described herein may also be implemented in electronic hardware, computer software, firmware, or any combination thereof. Such techniques may be implemented in any of a variety of devices such as general purposes computers, wireless communication device handsets, or integrated circuit devices having multiple uses including application in wireless communication device handsets and other devices. Any features described as modules or components may be implemented together in an integrated logic device or separately as discrete but interoperable logic devices. If implemented in software, the techniques may be realized at least in part by a computer-readable data storage medium comprising program code including instructions that, when executed, performs one or more of the methods described above. The computer-readable data storage medium may form part of a computer program product, which may include packaging materials. The computer-readable medium may comprise memory or data storage media, such as random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The techniques additionally, or alternatively, may be realized at least in part by a computer-readable communication medium that carries or communicates program code in the form of instructions or data structures and that can be accessed, read, and/or executed by a computer, such as propagated signals or waves.

The program code may be executed by a processor, which may include one or more processors, such as one or more digital signal processors (DSPs), general purpose microprocessors, an application specific integrated circuits (ASICs), field programmable logic arrays (FPGAs), or other equivalent integrated or discrete logic circuitry. Such a processor may be configured to perform any of the techniques described in this disclosure. A general purpose processor may be a microprocessor; but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Accordingly, the term "processor," as used herein may refer to any of the foregoing structure, any combination of the foregoing structure, or any other structure or apparatus suitable for implementation of the techniques described herein. In addition, in some aspects, the functionality described herein may be provided within dedicated software modules or hardware modules configured for encoding and decoding, or incorporated in a combined encoder-decoder (CODEC).

The specification and drawings are, accordingly, to be regarded in an illustrative rather than a restrictive sense. It will, however, be evident that various modifications and changes may be made thereunto without departing from the broader spirit and scope of the disclosure as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the disclosure to the specific form or forms disclosed, but on the contrary, the intention is to cover all modifications, alternative constructions and equivalents falling within the spirit and scope of the disclosure, as defined in the appended claims.

What is claimed:

1. A device to facilitate operations corresponding to radiological imaging, the device comprising:
one or more processors; and
memory communicatively coupled to the one or more processors and storing instructions which, when executed by the one or more processors, cause the device to perform operations comprising:
processing a request for one or more files and at least one image file received via a network by a network interface of the device, the at least one image file depicting a site of a subject, where the at least one image file was generated at least in part by an imaging device;
extracting site data and data associated with the subject from the request, the site data associated with the site of the subject depicted in the at least one image file;
generating a search string to execute with respect to a plurality of image files stored in one or more datastores to perform a search for one or more supplemental image files mapped to the subject based at least in part on the data associated with the subject;
consequent to the search, processing a set of results responsive to the search string, where the set of results comprises at least one supplemental image file mapped to the subject;
filtering the set of results using the site data to generate a subset of results from the set of results;
appending the subset of results to the at least one image file received via the network; and
causing transmitting of the subset of results appended to the at least one image file via the network to a second device.

2. The device to facilitate operations corresponding to radiological imaging as recited in claim 1, where the at least one supplemental image file mapped to the subject is associated with the site depicted in the at least one image file.

3. The device to facilitate operations corresponding to radiological imaging as recited in claim 2, where the generating the search string comprises generating one or more fuzzy search strings based at least in part on the data associated with the subject for execution of the search.

4. The device to facilitate operations corresponding to radiological imaging as recited in claim 3, where the one or more fuzzy search strings approximately match the data associated with the subject.

5. The device to facilitate operations corresponding to radiological imaging as recited in claim 1, where the at least one supplemental image file mapped to the subject is selected as relevant to the at least one image file based at least in part on the at least one supplemental image file depicting at least one additional site that is proximate to the site depicted in the at least one image file.

6. The device to facilitate operations corresponding to radiological imaging as recited in claim 1, where the generating the subset of results comprises narrowing at least one result from the set of results based at least in part on types of imaging devices that generated image files corresponding to the subset of results.

7. The device to facilitate operations corresponding to radiological imaging as recited in claim 1, where the operations further comprise prioritizing the subset of results based at least in part on modality data that indicates one or more types of imaging devices that generated image files corresponding to the subset of results.

8. A method to facilitate operations corresponding to radiological imaging, the method comprising:
processing a request for one or more files and at least one image file received via a network by a network interface of a device, the at least one image file depicting a site of a subject, where the at least one image file was generated at least in part by an imaging device;
extracting site data and data associated with the subject from the request, the site data associated with the site of the subject depicted in the at least one image file;
generating a search string to execute with respect to a plurality of image files stored in one or more datastores to perform a search for one or more supplemental image files mapped to the subject based at least in part on the data associated with the subject;
consequent to the search, processing a set of results responsive to the search string, where the set of results comprises at least one supplemental image file mapped to the subject;
filtering the set of results using the site data to generate a subset of results from the set of results;
appending the subset of results to the at least one image file received via the network; and
causing transmitting of the subset of results appended to the at least one image file via the network to a second device.

9. The method to facilitate operations corresponding to radiological imaging as recited in claim 8, where the at least one supplemental image file mapped to the subject is associated with the site depicted in the at least one image file.

10. The method to facilitate operations corresponding to radiological imaging as recited in claim 9, where the generating the search string comprises generating one or more fuzzy search strings based at least in part on the data associated with the subject for execution of the search.

11. The method to facilitate operations corresponding to radiological imaging as recited in claim 10, where the one or more fuzzy search strings approximately match the data associated with the subject.

12. The method to facilitate operations corresponding to radiological imaging as recited in claim 8, where the at least one supplemental image file mapped to the subject is selected as relevant to the at least one image file based at least in part on the at least one supplemental image file depicting at least one additional site that is proximate to the site depicted in the at least one image file.

13. The method to facilitate operations corresponding to radiological imaging as recited in claim 12, where the generating the subset of results comprises narrowing at least one result from the set of results based at least in part on types of imaging devices that generated image files corresponding to the subset of results.

14. The method to facilitate operations corresponding to radiological imaging as recited in claim 8, the method further comprising prioritizing the subset of results based at least in part on modality data that indicates one or more types of imaging devices that generated image files corresponding to the subset of results.

15. One or more non-transitory, machine-readable media having machine-readable instructions thereon which, when executed by one or more processing devices, cause the one or more processing devices to perform operations comprising:
- processing a request for one or more files and at least one image file received via a network by a network interface of a device, the at least one image file depicting a site of a subject, where the at least one image file was generated at least in part by an imaging device;
- extracting site data and data associated with the subject from the request, the site data associated with the site of the subject depicted in the at least one image file;
- generating a search string to execute with respect to a plurality of image files stored in one or more datastores to perform a search for one or more supplemental image files mapped to the subject based at least in part on the data associated with the subject;
- consequent to the search, processing a set of results responsive to the search string, where the set of results comprises at least one supplemental image file mapped to the subject;
- filtering the set of results using the site data to generate a subset of results from the set of results;
- appending the subset of results to the at least one image file received via the network; and
- causing transmitting of the subset of results appended to the at least one image file via the network to a second device.

16. The one or more non-transitory, machine-readable media as recited in claim 15, where the at least one supplemental image file mapped to the subject is associated with the site depicted in the at least one image file.

17. The one or more non-transitory, machine-readable media as recited in claim 16, where the generating the search string comprises generating one or more fuzzy search strings based at least in part on the data associated with the subject for execution of the search.

18. The one or more non-transitory, machine-readable media as recited in claim 17, where the one or more fuzzy search strings approximately match the data associated with the subject.

19. The one or more non-transitory, machine-readable media as recited in claim 15, where the at least one supplemental image file mapped to the subject is selected as relevant to the at least one image file based at least in part on the at least one supplemental image file depicting at least one additional site that is proximate to the site depicted in the at least one image file.

20. The one or more non-transitory, machine-readable media as recited in claim 15, where the generating the subset of results comprises narrowing at least one result from the set of results based at least in part on types of imaging devices that generated image files corresponding to the subset of results.

* * * * *